United States Patent
Elberse et al.

(10) Patent No.: US 9,440,047 B1
(45) Date of Patent: Sep. 13, 2016

(54) SYSTEMS AND METHODS FOR CATHETER TIP PLACEMENT USING ECG

(71) Applicants: Lambertus Wilhelmus Johannes Elberse, Oss (NL); Franciscus Ludovicus Maria Johannes Veldhuijzen, Liessel (NL); Raymond Lareau, Westford, MA (US); Mark Girard, Medway, MA (US); Damon Casiello, Lowell, MA (US)

(72) Inventors: Lambertus Wilhelmus Johannes Elberse, Oss (NL); Franciscus Ludovicus Maria Johannes Veldhuijzen, Liessel (NL); Raymond Lareau, Westford, MA (US); Mark Girard, Medway, MA (US); Damon Casiello, Lowell, MA (US)

(73) Assignee: AngioDynamics, Inc., Latham, NY (US)

(*) Notice: Subject to any disclaimer, the term of this patent is extended or adjusted under 35 U.S.C. 154(b) by 2 days.

(21) Appl. No.: 14/211,879

(22) Filed: Mar. 14, 2014

Related U.S. Application Data

(60) Provisional application No. 61/782,913, filed on Mar. 14, 2013, provisional application No. 61/928,112, filed on Jan. 16, 2014.

(51) Int. Cl.
*A61B 5/042* (2006.01)
*A61M 25/01* (2006.01)

(52) U.S. Cl.
CPC .. *A61M 25/0105* (2013.01); *A61M 2025/0166* (2013.01); *A61M 2205/3303* (2013.01); *A61M 2230/04* (2013.01)

(58) Field of Classification Search
CPC .......... A61B 5/04525; A61B 18/1492; A61B 2018/00357; A61B 18/00839; A61B 5/00; A61N 1/00
See application file for complete search history.

(56) References Cited

U.S. PATENT DOCUMENTS

| | | | |
|---|---|---|---|
| 4,362,166 A | 12/1982 | Furler et al. | |
| 4,577,634 A | 3/1986 | Gessman | |
| 4,644,960 A | 2/1987 | Johans | |
| 5,078,678 A | 1/1992 | Katims | |
| 5,121,750 A | 6/1992 | Katims | |
| 5,123,419 A | 6/1992 | Platt et al. | |
| 5,469,858 A | 11/1995 | Osborne | |
| 5,500,100 A | 3/1996 | Riley et al. | |
| 5,666,958 A | 9/1997 | Rothenberg et al. | |
| 5,709,210 A | 1/1998 | Green et al. | |
| 5,733,323 A | 3/1998 | Buck et al. | |
| 6,236,883 B1 * | 5/2001 | Ciaccio et al. | 600/515 |
| 6,368,285 B1 | 4/2002 | Osadchy et al. | |
| 6,892,091 B1 | 5/2005 | Ben-Haim et al. | |
| 6,973,346 B2 | 12/2005 | Hafer et al. | |
| 7,606,402 B2 | 10/2009 | Heimdal et al. | |

(Continued)

OTHER PUBLICATIONS

Jim Jenkins et al., "Computer diagnosis of supraventricular and ventricular arrhythmias. A new esophageal technique," Circulation, 60 (1979) 977-87.

(Continued)

*Primary Examiner* — Deborah Malamud
(74) *Attorney, Agent, or Firm* — Peter Flora

(57) ABSTRACT

A system and method for catheter placement using ECG is provided. In certain embodiments, the system and method can generate a patient specific window for tracking a characteristic of an ECG waveform, such as the amplitude of a P-wave. The patient specific window can be utilized in a system and method for assisting in the placement of a catheter within a patient. In other embodiments, a tip location algorithm can be used with an anti-thrombogenic catheter and an intravascular electrode assembly for maintaining a high resolution intravascular signal in an ECG based catheter tip placement system.

17 Claims, 10 Drawing Sheets

(56) References Cited

U.S. PATENT DOCUMENTS

| | | |
|---|---|---|
| 7,640,053 B2 | 12/2009 | Verin |
| 7,720,520 B2 | 5/2010 | Willis |
| 8,180,428 B2 | 5/2012 | Kaiser et al. |
| 8,280,498 B2 | 10/2012 | Jalde |
| 8,388,546 B2 | 3/2013 | Rothenberg |
| 8,512,256 B2 | 8/2013 | Rothenberg |
| 8,597,193 B2 | 12/2013 | Grunwald et al. |
| 8,965,490 B2 | 2/2015 | Lee et al. |
| 9,125,578 B2 | 9/2015 | Grunwald |
| 9,144,431 B2 | 9/2015 | Friedman et al. |
| 2004/0059237 A1 | 3/2004 | Narayan et al. |
| 2004/0097806 A1 | 5/2004 | Hunter et al. |
| 2006/0217655 A1 | 9/2006 | Vitullo et al. |
| 2007/0167738 A1 | 7/2007 | Timinger et al. |
| 2007/0197926 A1 | 8/2007 | Danehorn et al. |
| 2007/0299353 A1 | 12/2007 | Harlev et al. |
| 2008/0249375 A1 | 10/2008 | Obel |
| 2009/0099468 A1 | 4/2009 | Thiagalingam et al. |
| 2009/0177090 A1 | 7/2009 | Grunwald et al. |
| 2010/0049061 A1 | 2/2010 | Wilson et al. |
| 2010/0222664 A1 | 9/2010 | Lemon et al. |
| 2010/0317981 A1 | 12/2010 | Grunwald |
| 2010/0318026 A1 | 12/2010 | Grunwald |
| 2011/0208075 A1 | 8/2011 | Giese et al. |
| 2011/0213260 A1 | 9/2011 | Keel et al. |
| 2012/0059270 A1 | 3/2012 | Grunwald |
| 2013/0123597 A1 | 5/2013 | Rothenberg |
| 2013/0338517 A1 | 12/2013 | Rothenberg |
| 2014/0243659 A1 | 8/2014 | Rothenberg |

OTHER PUBLICATIONS

JM Jenkins et al., "Computer Diagnosis of Abnormal Cardiac Rhythms Employing a New P-Wave Detector for Interval Measurement," Computers and Biomedical Research, 11 (1978) 17-33.

SM Mohammad et al., "A Signals and Systems and Object Oriented Programming Approach to Development of ECG Analaysis Software," Computers in Cardiology, 29 (2002) 153-156.

Rangaraj M. Rangayyan, Biomedical Signal Analysis, IEEE Press pp. 64-66.

Dilaveris, P.E., P-Wave Dispersion: A Novel Predictor of Paroxysmal Atrial Fibrillation, Annals of Noninvasive Electrocardiology, 6: 159-165.

G K Feld, Radiofrequency catheter ablation for the treatment of human type 1 atrial flutter. Identification of a critical zone in the reentrant circuit by endocardial mapping techniques., 86: 1233-1240.

\* cited by examiner

SYSTEMS AND METHODS FOR CATHETER TIP PLACEMENT USING ECG

CROSS-REFERENCE TO RELATED APPLICATIONS

This application claims priority to U.S. Provisional Application No. 61/782,913, filed on Mar. 14, 2013 and titled Method for Locating a Catheter Using Intracardial ECG, and U.S. Provisional Application No. 61/928,112, filed on Jan. 16, 2014 and titled Systems and Methods for High Clarity Signal Acquisition from a Catheter Lumen, both of which are incorporated herein by reference in their entireties.

FIELD OF THE INVENTION

The present invention relates generally to positioning a catheter tip within a human body. More specifically, the invention relates to systems and methods that utilize ECG for assisting with catheter tip placement procedures.

BACKGROUND OF THE INVENTION

Medical professionals commonly use catheters for gaining prolonged access to an area within the body. Once the catheter tip is positioned at the target location, treatments such as antibiotics, chemotherapy, pain medicine, and nutrition can be administered. If the catheter tip is improperly positioned during insertion, various risks to the patient arise, including a fluid infusion that causes pain or injury to the patient, complications due to increased thrombosis rates, delays in therapy, catheter malfunction and additional costs.

General standards for proper catheter insertion depend on the type of catheter and the treatment being provided. For example, peripherally inserted central catheters (or PICC lines) are commonly inserted into a brachial, cephalic or basilic vein in the arm and advanced through the venous system towards the superior vena cava (SVC). Current medical standards recommend that the distal tip of the catheter terminate in the lower % of the SVC, close to the junction of the SVC and the right atrium (RA). However, since PICCs are commonly inserted into a vein in the arm and advanced through the venous system to reach the SVC, the PICC line tip may be inadvertently positioned in a non-target area, such as the internal jugular, the subclavian vein, or too far past the SVC-RA junction and into the heart.

Catheter tip location techniques have improved the ability of medical professionals to verify the location of the catheter tip. One technique uses fluoroscopy to confirm tip location. Fluoroscopy provides the operator with real-time images of the patient's anatomy using a fluoroscope. Another technique uses a combination of an electromagnetic beacon and an electromagnetic detection element to track the beacon positioned near the catheter tip. Many techniques have also been described for using electrocardiography (ECG) to assist with catheter tip placement by measuring an ECG signal from an intravascular (IV) electrode positioned at or near the catheter tip.

Tracking ECG waveform changes measured from an IV electrode as the catheter advances through the vasculature towards the SA node can provide valuable feedback to the medical professional placing the catheter, since the SA node is located near the SVC-RA junction. Specifically, tracking the P-wave morphology is known to be a valuable tool. For example, as the IV electrode advances down the SVC towards the SA node, the amplitude of the P-wave will start to rise. The amplitude of the P-wave will eventually peak when the IV electrode is closest to the SA node, and eventually start to decrease in amplitude as the IV electrode moves away from the SA node and enters the RA. Observation of this phenomenon has been utilized by medical professionals for catheter placement procedures at least as early as the mid-20$^{th}$ century.

Automated systems that track P-wave morphology for catheter tip placement have also been previously described. For example, in U.S. Pat. No. 5,121,750 to Katims, incorporated herein by reference, a monitoring system detects changes in the P-wave as measured from an IV electrode for providing automated user instructions on catheter placement. The monitoring system (1) detects increases in the P-wave amplitude as the IV electrode approaches the SA node and signals the user to continue advancing the catheter, (2) detects a decrease in the P-wave amplitude as the IV electrode passes the SA node and signals the user to pull back the catheter, and (3) detects that the P-wave is within a certain range of the maximum and signals the user to stop once within that range.

For tip positioning systems that rely on tracking changes in P-wave amplitude for providing user feedback, several obstacles may arise. For instance, P-wave location and morphology can change from patient to patient based on a number of factors (explained in further detail below). It would be beneficial for an ECG and P-wave based tip location system to have a more patient specific analysis approach to account for patient-to-patient variability. Further, ECG signals from IV electrodes tend to have low resolution due to a number of factors, including electrode downsizing and design limitations, movement, and pickup of physiologic and extraphysiologic artifacts. A noise spike may cause the algorithm to misinterpret the acquired signal, possibly leading to erroneous user feedback. Systems that can accurately provide user feedback, manage lower resolution IV electrode signals, and minimize the influence of ECG artifacts on signal processing would be advantageous.

Further, problems such as thrombus buildup at the catheter tip and within the catheter lumen can affect IV ECG signal acquisition. Thrombus buildup can partially block electrode exposure which can result in a muted signal. Further, thrombus buildup in contact or near the electrode can cause the IV ECG signal to refract off of the thrombus formations, adding noise to the IV ECG waveform. To clear the catheter lumen and opening of thrombus, and to combat the formation of new thrombus, the catheter lumen can be flushed with saline. However, this can add time and cost to the procedure. Further, prolonged interruptions in catheter advancement may interfere with the normal execution of the tip location algorithm, and may prevent the algorithm from properly executing, or lead to erroneous user feedback.

Improved catheter tip placement systems and methods for overcoming these issues is desired.

SUMMARY OF THE INVENTION

The invention is directed to a system and method for catheter tip placement using ECG. In one aspect, the invention is a system and method for establishing an ECG search window for catheter tip placement. In another aspect, the invention is a system and method for assisting in the placement of a catheter within a patient. In yet another aspect, the invention is a system and method for high clarity signal acquisition in tip location systems utilizing an intravascular electrode. In certain aspects, a method for establishing an ECG search window for a catheter tip placement system includes the steps of acquiring multiple surface ECG signals from at least one surface ECG electrode; generating a signal averaged surface ECG signal from the multiple surface ECG signals; determining a first fiducial point by identifying an extremum within the signal averaged surface ECG signal; establishing a first ECG search window between first and second predetermined values offset from the first fiducial point; determining a second fiducial point by identifying an extremum in the first ECG search window; determining a search window beginning value by identifying a local extremum on a first side of the second fiducial point, and determining a search window ending value by identifying a local extremum on a second side of the second fiducial point; and establishing a second ECG search window between the search window beginning value and the search window ending value so that the second ECG search window is narrower than the first ECG search window.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 3A shows a normal P-wave; FIG. 3B shows a P-wave with a higher initial positive deflection; FIG. 3C shows a P-wave with a notch near the peak; FIG. 3D shows a prolonged P-wave; FIG. 3E shows an offset P-wave; FIG. 3F shows a spike artifact followed by a normal P-wave;

FIG. 4A illustrates a 3 surface electrode configuration; FIG. 4B illustrates a 4 surface electrode configuration; FIG. 4C illustrates a 3 surface electrode configuration with an IV electrode;

FIG. 8A is a graphical view of a GUI command to move forward; FIG. 8B is a graphical view of a GUI command to move backward; FIG. 8C is a graphical view of a level indicator GUI command to stop; and FIG. 8D is a graphical view of a GUI including user commands, IV ECG waveforms and surface ECG waveforms;

FIG. 9A is a perspective view of a conventional catheter coaxially surrounding a stylet; FIG. 9B is a side view of a conventional catheter with thrombus buildup;

FIG. 11A is a perspective view of the catheter tip and stylet system; FIG. 11B is a cross-sectional view of the catheter tip and stylet system.

DETAILED DESCRIPTION OF THE INVENTION

Figure 1:
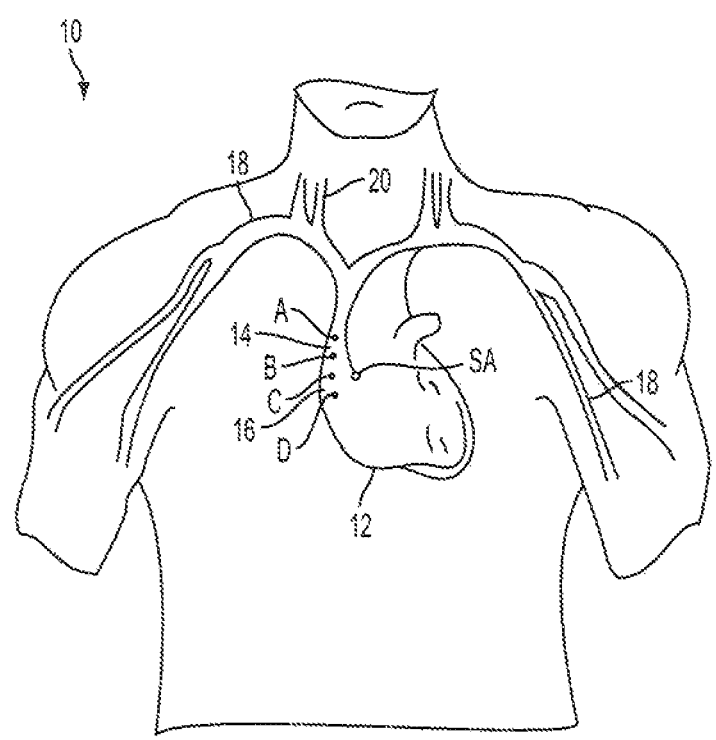
FIG. 1 is a diagram of an upper portion of a human body illustrating various positions of the vasculature, including the SVC, RA and SA node.

The present invention can be understood more readily by reference to the following detailed description, the examples included therein, and to the Figures and their following description. The drawings, which are not necessarily to scale, depict selected preferred embodiments and are not intended to limit the scope of the invention. The detailed description illustrates by way of example, not by way of limitation, the principles of the invention. The skilled artisan will readily appreciate that the devices and methods described herein are merely examples and that variations can be made without departing from the spirit and scope of the invention. It is also to be understood that the terminology used herein is for the purpose of describing particular embodiments only and is not intended to be limiting. Systems and methods described below are compatible with ECG assisted placement for a variety of medical devices, including for example PICCs, central venous catheters, midline catheters, port catheters, and dialysis catheters.

Referring now in detail to the drawings, in which like reference numerals indicate like parts or elements throughout the several views, in various embodiments, presented herein are systems and methods for catheter tip placement using ECG.

As described above, catheters such as PICC lines are commonly inserted into a brachial, cephalic or basilic vein in the arm and advanced through the venous system towards the SVC-RA junction with the goal of having the catheter tip terminate in the lower % of the SVC. As shown in FIG. 1, a human body 10 has a vasculature system 18 leading to the heart 12. Using P-waves as a guidance measure and the SA node (SA) as a reference point, an IV electrode located near a PICC tip can track changes in the P-wave generated from the SA node (SA) as the PICC tip and IV electrode advance towards the SVC 14 and the RA 16. As described in Katims, an algorithm can be employed to detect increases in P-wave amplitude as the IV electrode advances from positions A to B, and then B to C. When the IV electrode passes the SA node (SA) and moves from position C to D, the algorithm detects a decrease in P-wave amplitude and a user command can be given indicating that the PICC be pulled back until either the maximum P-wave is reached again, or until a percentage of the maximum P-wave is detected. If, for example, the algorithm detects a severe and premature drop in P-wave amplitude during insertion, or if the P-wave never meets an incrementing threshold, that could indicate that the PICC tip accidently migrated up to the internal jugular 20 instead of down towards the SVC 14.

Figure 2:
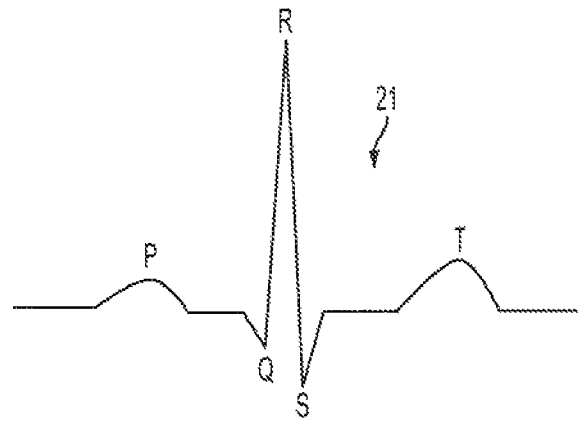
FIG. 2 is an exemplary ECG waveform showing typical shapes and positions of common ECG waves.

For tip location systems that rely on an algorithm to interpret changes in P-waves, the ability of the system to accurately identify the P-wave given patient-to-patient P-wave variability and noise are important to system reliability and accuracy. As shown in FIG. 2, the P-wave is not typically the most prominent wave in an ECG waveform. The QRS complex is typically the most prominent waveform and is therefore considered the simplest to detect, primarily because of the sharp delineation of the R-wave. Other waves, such as the T-wave or the U-wave (not shown) may also present as prominent or diminished depending on various factors.

Figure 3A:
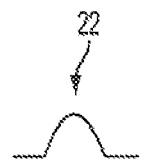
FIGS. 3A-3F are exemplary P-wave morphologies.
Figure 3B:
Figure 3C:
Figure 3D:
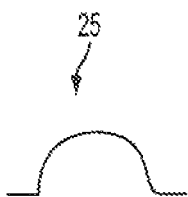
Figure 3E:
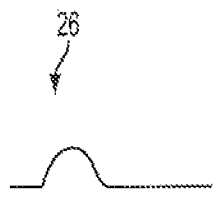

Patient variability in P-wave morphology is not uncommon. FIGS. 3A-3F illustrate just a few common examples of P-wave morphologies. A normal P-wave is illustrated in FIG. 3A. A normal P-wave 22 is formed in part by the combination of right and left atrial depolarization waves in sequence. The P-wave 23 illustrated in FIG. 3B shows a higher initial positive deflection, which could be caused by right atrial enlargement, leading to a more pronounced peak during right atrial depolarization. Right atrial enlargement is common in patients suffering from pulmonary hypertension. Left atrial enlargement could cause a P-wave 24 with a notch near the peak as shown in FIG. 3C, or a prolonged P-wave 25 as shown in FIG. 3D. P mitrale or a notched P-wave may also be due to mitral stenosis. An offset P-wave 26 as shown in FIG. 3E could result in patients having atrial fibrillation or extrasystoles. Numerous other factors including respiratory rate, heart rate, prior surgeries (e.g. a MAZE procedure), or patient conditions (e.g. ventricular tachycardia, Wolff-Parkinson-White syndrome or atrial disease) could impact P-wave morphology and patient variability.

Figure 3F:
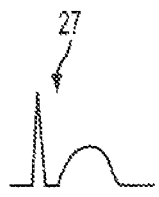

Even if a patient presents a normal P-wave, an artifact such as the spike artifact shown in the P-wave 27 of FIG. 3F could appear near or on top of the P-wave, leading to a misinterpretation of the P-wave amplitude during signal processing. In general, artifacts can be generated from physiologic or extraphysiologic sources, such as patient movement, electrical noise from other parts of the body, and interference from medical equipment and other sources of electrical disturbance in the local environment. Systems and methods according to the present invention improve P-wave and ECG based tip location systems as described further below.

Figure 4A:
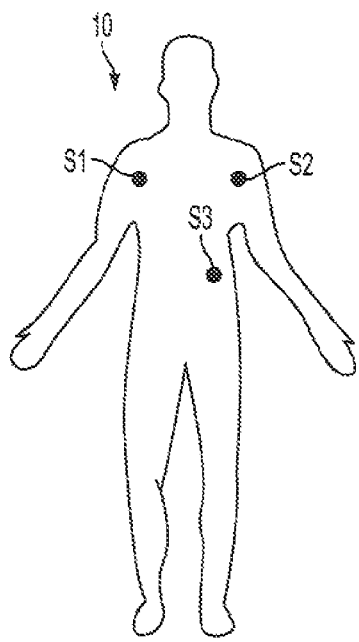
FIGS. 4A-4C are diagrams of a human body illustrating various surface electrode configurations according to exemplary embodiments of the invention.
Figure 4B:
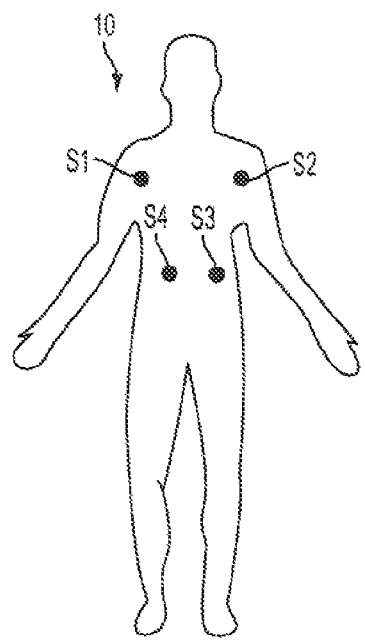

According to an embodiment of the invention, multiple surface electrodes and a single IV electrode are utilized for ECG signal acquisition. Alternative embodiments may utilize a single surface electrode or multiple IV electrodes. In this exemplary embodiment and as illustrated in FIG. 4A, three surface electrodes S1, S2, S3 are placed on a surface on the skin of the patient 10 to acquire a surface ECG waveform. This configuration, utilizes an right arm (RA—white) lead S1, a left arm (LA—black) lead S2, and a left leg (LL—red) lead to form what is commonly referred to as Einthoven's Triangle. In an alternative embodiment, an additional neutral lead (N) S4 can be positioned as a right leg lead 84, as shown in FIG. 4B. An IV electrode IV1 will also be utilized by the system for acquiring an IV ECG signal as the IV electrode is advanced through the vasculature.

Figure 4C:
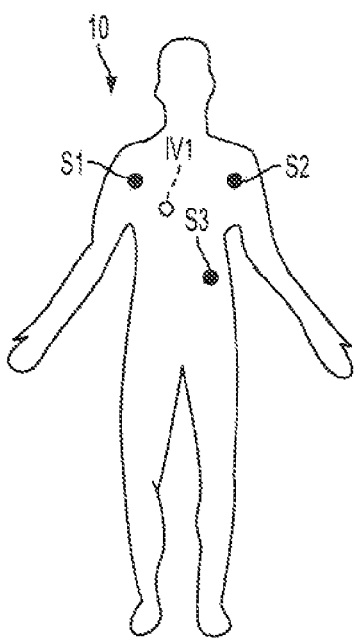
Figure 5:
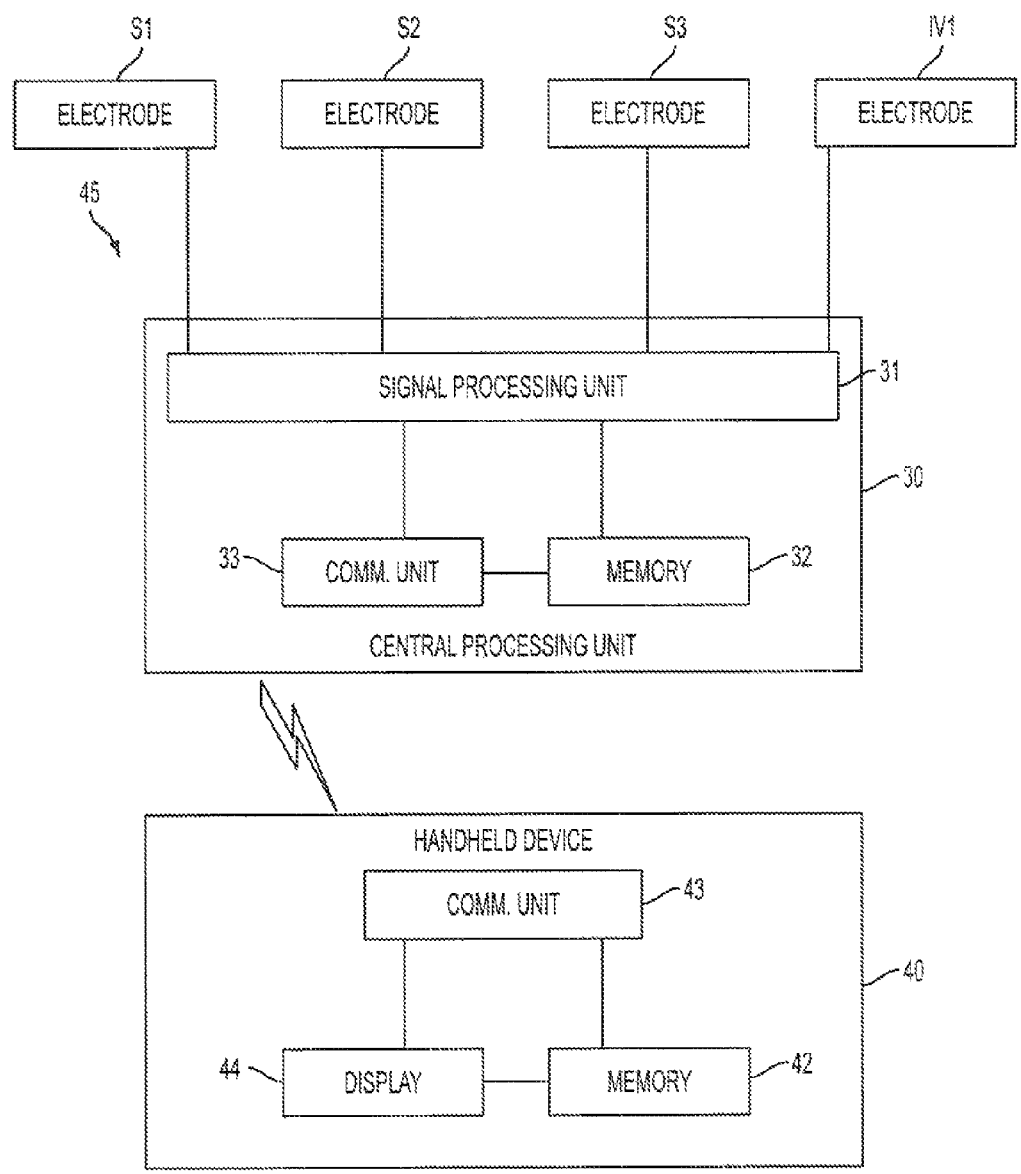
FIG. 5 is a diagram of a catheter tip placement system according to an exemplary embodiment of the invention.

As shown in the system diagram of FIG. 5 (and using the example configuration shown in FIG. 4C), all of the electrodes S1, S2, S3, IV1 are operably connected to a central processing unit 30 of the tip location system 45. The three surface ECG electrodes S1, S2, S3, and the IV electrode IV1 connect to a signal processing unit 31, where the signals are acquired and processed by the tip location algorithm. A memory unit 32 can be used to store data including waveforms, algorithm variables and error messages. The communication unit 33 on the central processing unit 30 can transmit data via a hardwired or wireless connection to a communication unit 43 on a handheld device. The handheld device 40 can be for example a smart phone or a table. Alternatively, this device 40 can be a unit mounted on a pole or otherwise stationary in the medical suite. A display 44 such as a touch-screen display can be integral to the handheld device, which communicates with the communication unit 43 and a memory unit 42. The display can communicate user feedback to the medical professional performing the procedure, such as catheter advancement instructions, ECG waveforms and error messages. A touch-screen on the display can be used to communicate information between the medical professional and the tip location system 45. In alternative embodiments, the central processing unit 30 and the handheld device 45 are a single integral unit forming the tip location system 45.

Figure 6:
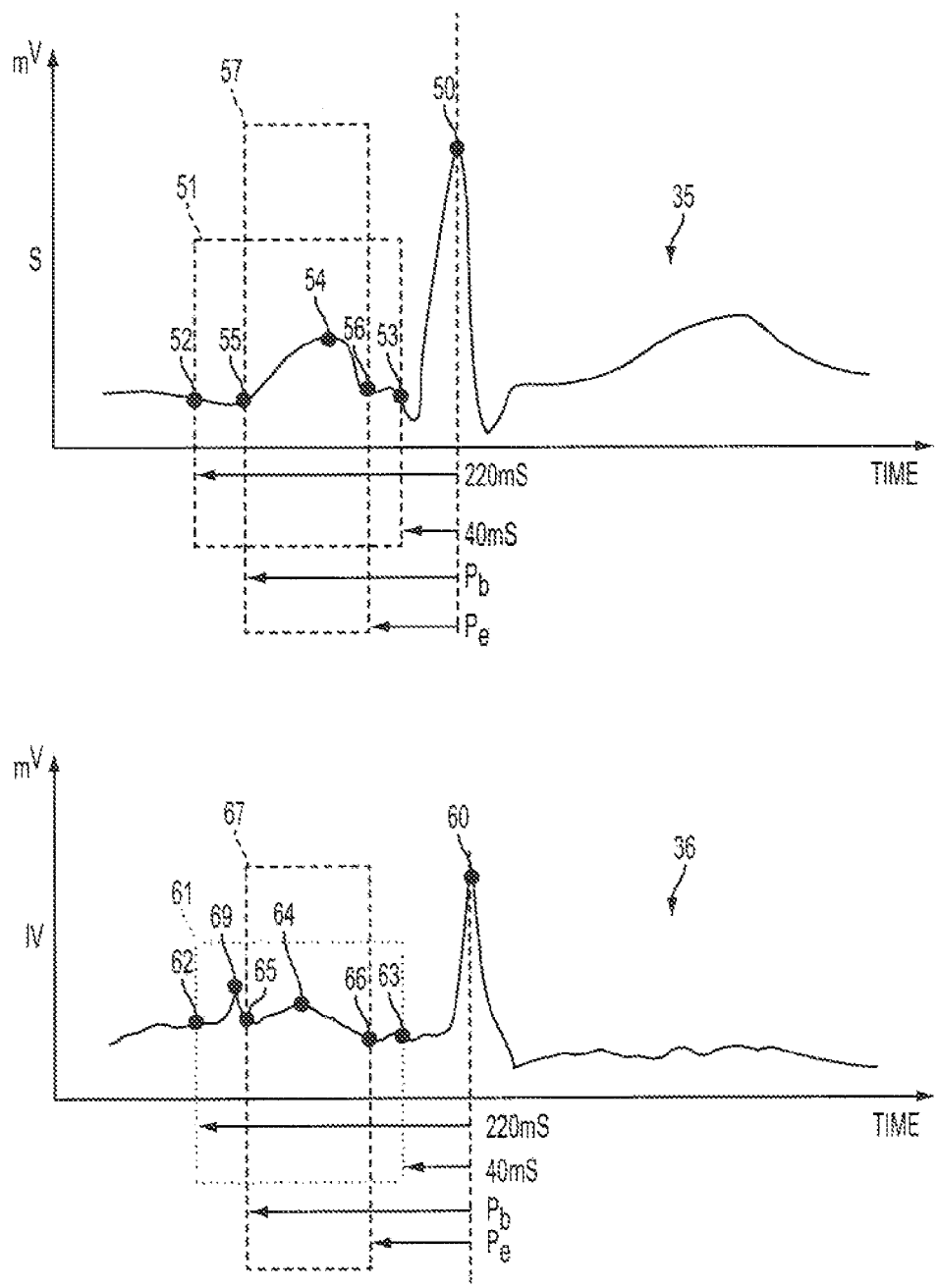
FIG. 6 is a set of waveforms diagram showing a search window generated according to a surface ECG waveform and overlaid onto an IV ECG waveform according to an exemplary embodiment of the invention.

A customized and patient specific IV ECG search window can be established under the following method according to an exemplary embodiment of the invention. For signal acquisition, the patient is prepped with an electrode configuration as illustrated in FIG. 4C. Now, with reference to FIG. 6, a surface ECG waveform 35 is acquired from surface ECG electrodes. The surface ECG waveform 35 can represent a single heartbeat cycle as measured directly from one ECG electrode, a waveform that has been averaged among measurements from multiple surface ECG electrodes (e.g. Wilson's central terminal), a signal averaged waveform from one or more surface ECG electrodes averaged over multiple heartbeats, a waveform run through a filter, or a combination of the above to increase the waveform resolution. In a preferred embodiment, the surface ECG waveform 35 is a signal averaged waveform, averaged from multiple surface ECG electrodes and further averaged over 10-20 heartbeats. Once the signal averaged surface ECG waveform 35 has been generated, it is analyzed to find the peak of the R-wave 50 as an initial fiducial point. A number of R-wave or QRS detection algorithms known in the art can be incorporated for this purpose, including Pan Tomkins, Hilbert transformation, wavelet coefficient estimation, linear filtering and model based approaches. Alternative fiducial points such as the onset or offset of the R-wave, the Q-wave or the S-wave can also be used.

After the peak of the R-wave 50 is identified, an initial P-wave search window 51 is established based on a generalized area of where the P-wave can be expected to appear in all patients, accounting for P-wave variability between patients. In this embodiment, two predetermined points, 220 ms (52) prior to the R-wave peak 50 and 40 ms (53) prior to the R-wave peak 50 form the beginning and ending of the initial P-wave search window 51. Other predetermined points, which may range for example between 20-60 ms and 200-240 ms can be used. With the initial P-wave search window 51 now established, the peak of the P-wave 54 is identified as the absolute peak within the initial P-wave search window 51. Isolated noise, interference, and aberrant spikes will be filtered out of the surface ECG waveform 35 during the signal averaging step, minimizing the possibility that they will falsely present as the absolute peak within the initial P-wave search window 51.

Using the peak of the P-wave 54 as a second fiducial point, the first local minima to the left 55 and right 56 sides of the peak of the P-wave 54 are identified to form the bounds of a patient specific surface ECG P-wave window 57. A first variable Pb represents the beginning of the surface ECG P-wave window 57 based on the distance between the minimum to the left side 55 of the peak of the P-wave 54 and the R-wave 50. A second variable Pe represents the end of the surface ECG P-wave window 57 based on the distance between the minimum to the right side 56 of the peak of the P-wave 54 and the R-wave 50. In alternative embodiments, it could be advantageous to expand one or more edges of the patient-specific P-wave window to a subsequent second or third local minimum. For example, the system might initially identify a notch in the P-wave (see for example FIG. 3C) as the first local minimum (to the left or right of the P-wave peak). In this case, sensing that the first left or right local minimum is in too close in proximity (in amplitude or time) to the P-wave peak, the system may recognize a false edge of the P-wave and expand the window to a subsequent local minimum, generating a more relevant P-wave window for that particular patient. In yet another alternative embodiment, edges of the patient specific P-wave window can be established based on a predetermined distance surrounding the P-wave peak. Further, patient specific P-wave window edges can be further expanded or narrowed to deal with a number of factors, including P-wave morphology or noise in signal. Other windows described herein can be further modified in a similar fashion.

Once the patient specific surface ECG P-wave window 57 is established using the surface ECG waveform 35, it can be overlaid onto the IV ECG waveform 36 to form a patient specific IV P-wave search window 67. To generate the IV P-wave search window 67, the R-wave 60 in the IV ECG waveform 36 is first identified using a QRS complex or R-wave detection technique. Then, Pb and Pe, determined from analysis of the surface ECG, are offset to the left of the R-wave 60, establishing the beginning 65 and ending 66 of the IV P-wave search window 67. This technique allows the system to establish a patient specific IV P-wave search window using the higher resolution surface ECG waveform, then transfer the surface ECG P-wave search window to the lower resolution IV ECG signal for more accurate signal processing during the catheter placement procedure. If, in this example, a generic non patient specific search window 61 was applied to the IV ECG waveform 36 with non patient specific beginning 62 and ending 63 points, an artifact spike 69 would have presented as the local maximum, throwing off the tip location algorithm which relies on tracking the P-wave amplitude 64. Using this method, the only wave in the lower resolution IV ECG waveform 36 that needs to be specifically identified is the R-wave 60, which is sharply delineated even in lower resolution ECG waveforms. This improved tip location ECG signal processing technique allows for consistent identification of the P-wave in the lower resolution IV ECG waveform, and provides a technique that is efficient enough to run in real time for live user feedback during the catheter placement procedure.

It is important to note that the ECG waveform may appear as inverted depending on a number of factors affecting waveform polarity, including for example ECG lead configuration, whether or not the signal acquisition equipment is set to invert acquired signals, and physical abnormalities changing normal electrophysiological conduction paths. Thus, for example, if the surface ECG waveform 36 shown in FIG. 6 was inverted, the R-wave peak 50 and the P-wave peak 54 would present as minimums instead of maximums. The method described above for customizing a patient specific IV ECG search window can be adjusted to detect waveforms presenting as either local minimums or local maximums since either type of extremum can just as easily be located and tracked. Adjustments for changing the type of extremum being tracked can happen automatically using a simple test algorithm such as a peak detection or baseline analysis algorithm. Alternatively, the system can measure absolute values of extrema so that the displacement of the deflection, and not the positive or negative value of the deflection becomes the relevant measure.

Figure 7A:
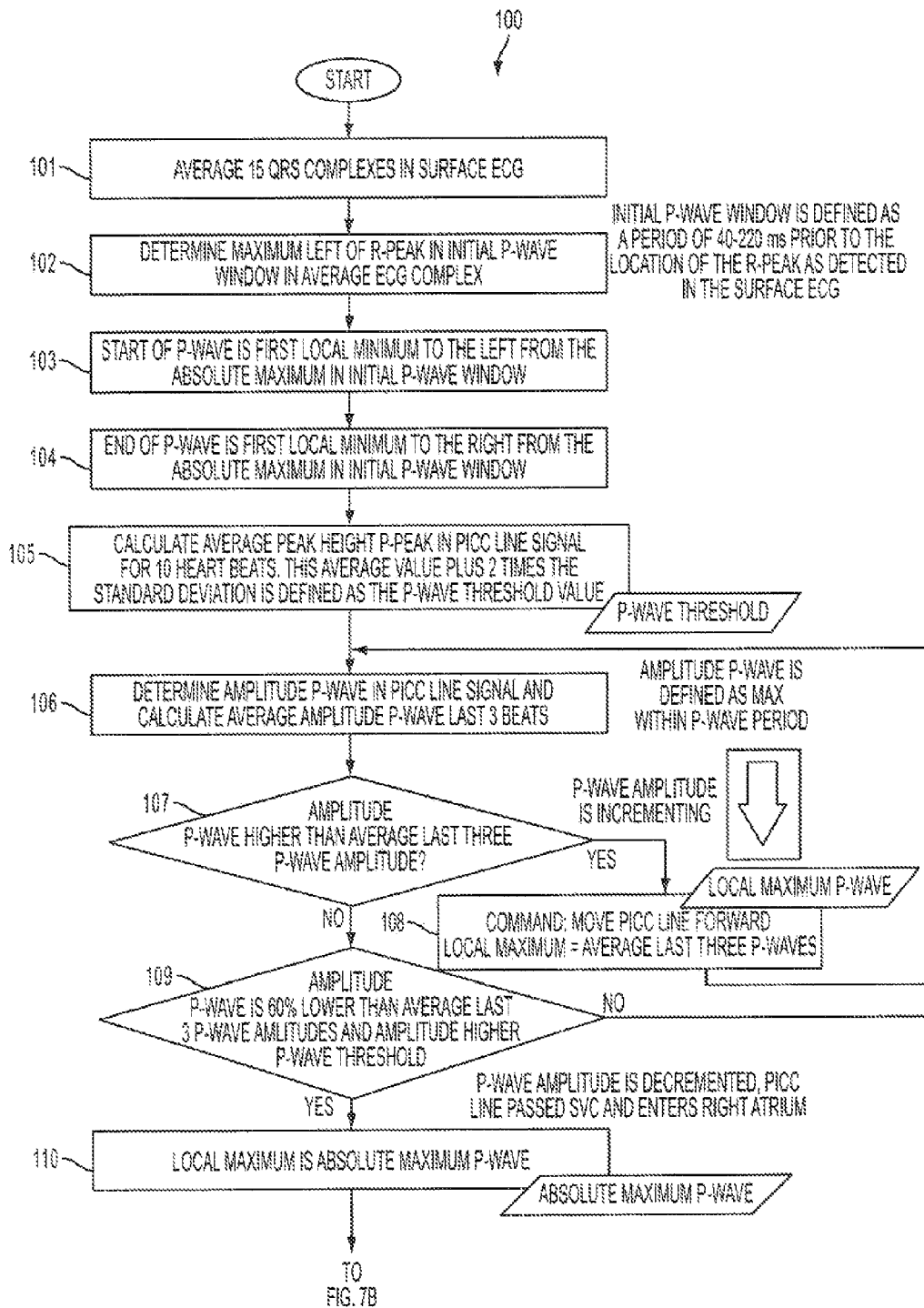
FIGS. 7A and 7B show a flow chart for a tip location algorithm according to an exemplary embodiment of the invention.
Figure 7B:
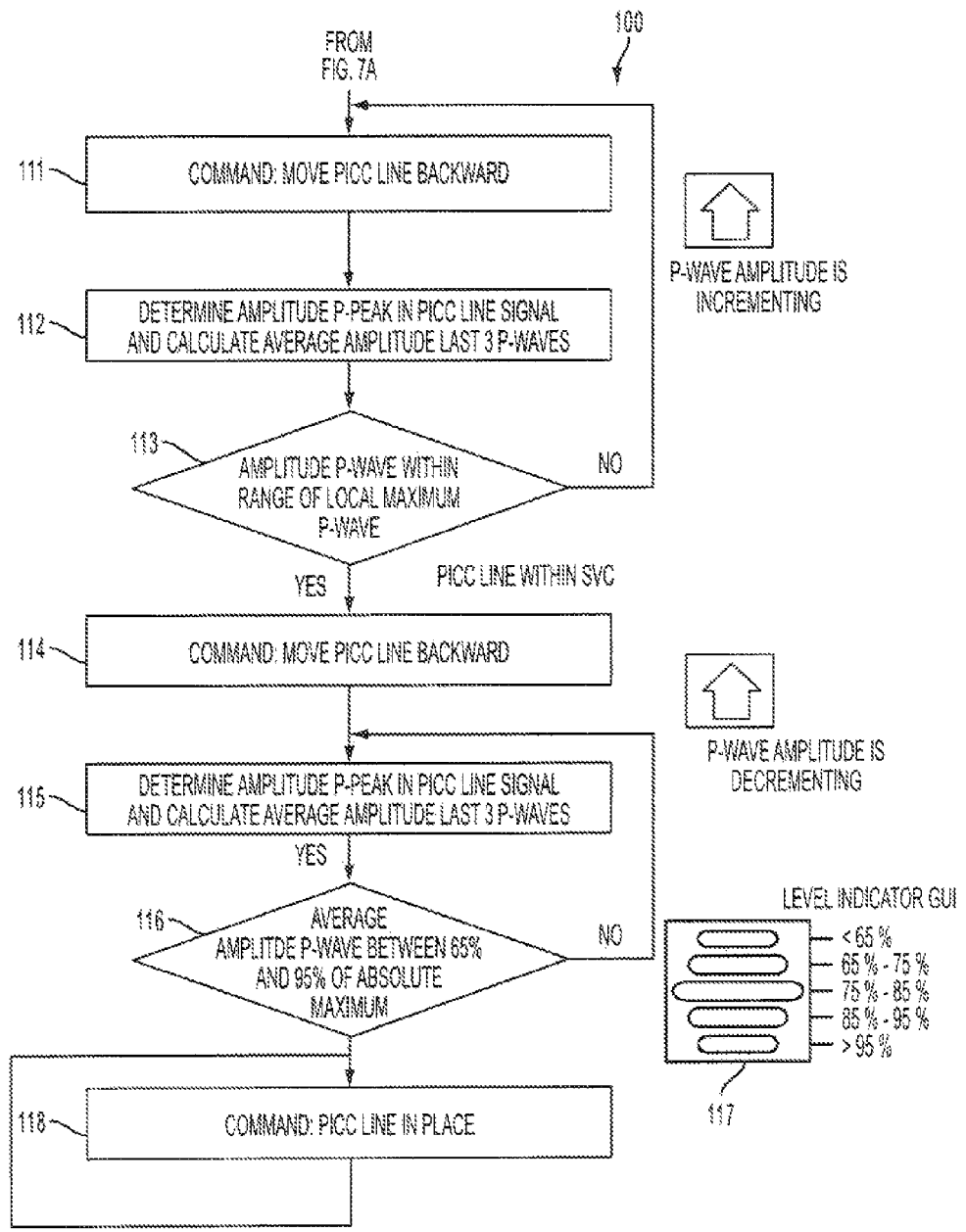
Figure 8A:
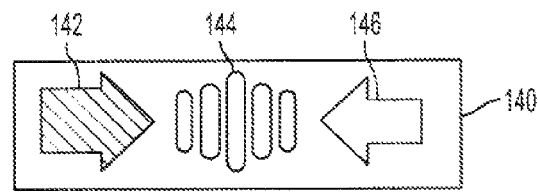
FIGS. 8A-8D show a tip location user feedback graphical user interface (GUI) according to an exemplary embodiment of the invention.
Figure 8B:
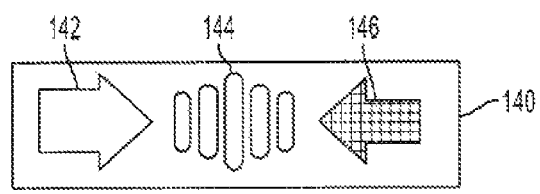
Figure 8C:
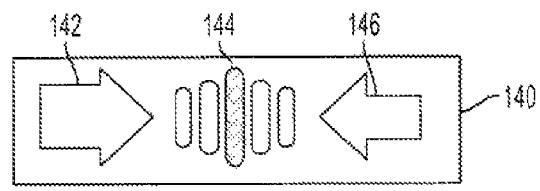
Figure 8D:
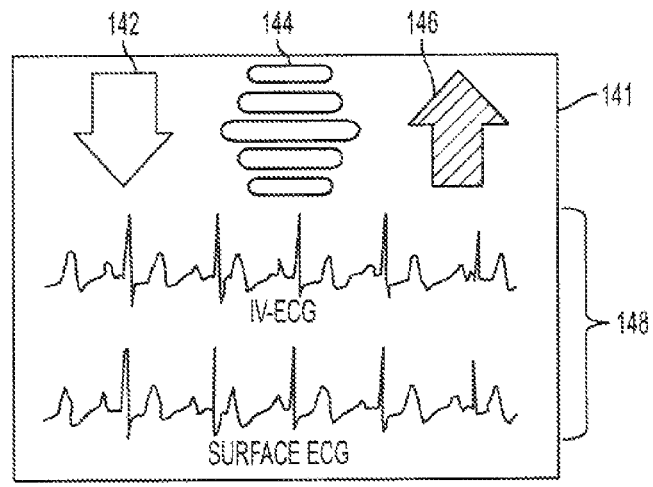

An algorithm for placing a PICC line according to an exemplary embodiment of the invention is now explained with reference to the flow chart 100 shown in FIGS. 7A and 7B. First, with reference to FIG. 7A, a surface P-wave window is established in similar fashion to the method described above. ECG signals are acquired from surface ECG electrodes to create a signal averaged surface ECG signal 101, and the QRS complex is identified. The initial window for finding the P-wave is determined by looking to the left of the R-peak at the period between 40-220 ms prior to the R-wave peak 102. The peak of the P-wave is identified by finding the absolute maximum of the signal averaged surface ECG in the initial P-wave window. To find a beginning value for a patient specific P-wave window, the algorithm first looks at the surface ECG signal left of the P-wave peak and identifies the first local minimum 103. Similarly, to find an ending value for the patient specific P-wave window, the first local minimum right of the P-wave peak is identified 104. The identified left and right local minimums provide the beginning and ending values for a patient specific window that can now be applied to P-wave analysis in the IV ECG signal as explained above with reference to FIG. 6. A "P-wave threshold" value is also calculated and saved in memory for reference later on in the algorithm (explained in further detail below), and is calculated as the average P-wave amplitude over 10 heartbeats plus two times the standard deviation 105.

Next, a series of steps for providing user instruction during the PICC placement procedure are executed based on P-waves acquired from the IV ECG electrode located at or near the tip of the PICC. The algorithm begins to track changes in the P-wave amplitude by looking at the amplitude of the waveform within the patient specific IV P-wave window 106. A decision is made based on how the IV ECG P-wave amplitude changes 107. If the P-wave amplitude is higher than the average of the most previous three P-wave amplitudes, then that indicates that the P-wave is incrementing, and the user is told to advance the PICC forward 108. A "local maximum P-wave" value is calculated and saved in memory as the average of the last three P-waves, and the algorithm loops back to determine again whether or not the current P-wave amplitude is higher than the average of the most previous three P-wave amplitudes. The user command to advance will typically be repeated for multiple cycles, as the IV electrode approaches the SA node. Alternatively, if a current P-wave amplitude is lower than the average of the most previous three P-wave amplitudes, a further decision is made as to whether or not the amplitude of the P-wave is 60% lower than the average of the last three P-waves, and whether or not the amplitude of the P-wave is higher than the P-wave threshold 109. The 60% threshold is for determining if the drop in the P-wave was significant, indicating that the SA node may have been passed. However, a second check against the P-wave threshold value is to ensure that the drop in the P-wave is at the very least above the P-wave threshold amplitude recorded when the IV electrode was positioned much further away from the SA node at the beginning of the procedure. A more dramatic drop in the P-wave amplitude may otherwise indicate an issue, such as a signal acquisition error or a problem with the patient's physiological activity. If both the amplitude of the P-wave is 60% lower than the average of the last three P-waves and higher than the P-wave threshold, the algorithm determines that the absolute maximum P-wave has been reached. The most recent "local maximum P-wave" value becomes the "absolute maximum P-wave" value, and is saved in memory 110. At this point, user feedback instructs the user to move the PICC line backwards 111, and the amplitude of the P-wave is measured and the average amplitude of the three most recent P-waves are calculated 112.

The next series of steps determines user feedback for moving the PICC line and IV electrode backwards to the target site. First, the algorithm instructs the user to pull back the PICC line until the averaged P-wave amplitude is within a particular range of the "local maximum P-wave" amplitude 113. An incrementing P-wave is now being tracked. When the P-wave amplitude is within range, the user is instructed to continue to move the PICC line backwards 114. The amplitude of the P-wave continues to be measured and the average amplitude of the three most recent P-waves is calculated 115. A decreasing P-wave amplitude is now tracked, and a decision is made regarding whether or not the average amplitude enters the range of 75%-85% of the "absolute maximum P-wave" 116. The current range is indicated by the center bar on a level indicator GUI 117. If the average amplitude is within the 75%-85% range, the user is notified that the PICC tip is at the target location 118. If not, the algorithm loops back to tracking the decrease in averaged P-wave amplitude. If the user pulls back too far, the algorithm can automatically loop back to an earlier advance state, or a restart feature can return the algorithm back to the beginning. In addition, the system can be modified so that the center bar reflects particular ranges that correspond with the type of procedure being performed or the type of catheter being placed. So for example, if the target location for the catheter tip is further up the SVC, the center bar may be set to a 65-75% range. Alternatively, if the target location for the catheter tip is further down into the RA, the algorithm can be modified so that the user is instructed to stop once the decrementing P-wave amplitude reaches a particular range after hitting the maximum P-wave.

Now with reference to FIGS. 8A-8D, examples of GUIs 140, 141 for user feedback are shown. Graphical instructions such as arrows, words, colors, or other symbols indicating advance PICC 142 or pull back PICC 146 could signal an instruction to the user. Alternatively or concurrently, audio commands can be utilized. The GUI 140, 141 could be part of a touch screen handheld device, such as a smart phone or a tablet. A GUI showing level indicators 144 can also be included. Waveforms of the surface ECG and IV ECG signals can also run on the screen so that the user can monitor the resolution of the signal and the ECG status of the patient.

In certain embodiments, a tip location procedure record is generated after each procedure for the patient's record. The tip location procedure record could record information including: (1) patient background information, including name, date of birth, a patient ID number, a catheter description, a user ID and miscellaneous notes; (2) a graphical display of ECG waveforms time stamped at various decision points, such as verification of an acceptable surface ECG waveforms, advance ECG waveforms, pull back ECG waveforms, and a stop at target ECG waveforms; and (3) a post procedure questionnaire assessing the procedure, the patient, and any other relevant factors. The record could be saved electronically, printed out, or sent transmitted wirelessly to a local or remote server or database.

Figure 9A:
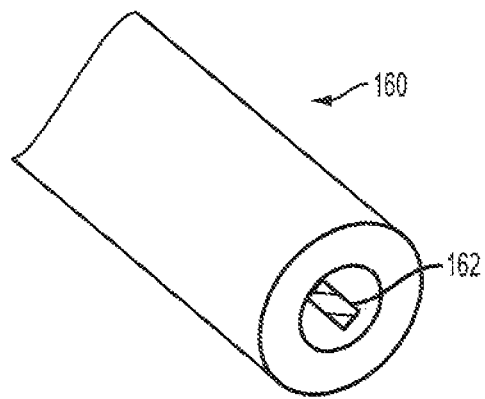
FIGS. 9A and 9B are prior art figures showing a conventional catheter.

As mentioned above, tip location systems often use a stylet to track changes in the P-wave as the stylet advances towards the SA node. The stylet may be similar to a conventional guidewire, or it could be a specialty stylet with a plurality of electrodes, such as bipolar electrodes disposed at different locations along the stylet. As shown in prior art FIG. 9A, the distal tip of a catheter 160 can have a stylet 162 positioned at or near the distal opening for acquiring an IV ECG signal. The stylet 162 acts as an electrode and transmits the physiological ECG signal propagated from the SA node from the catheter tip to a proximal connection element such as an alligator clip. The alligator clip is operably connected to the tip location system for signal processing and interpretation of the IV ECG signal.

Figure 9B:
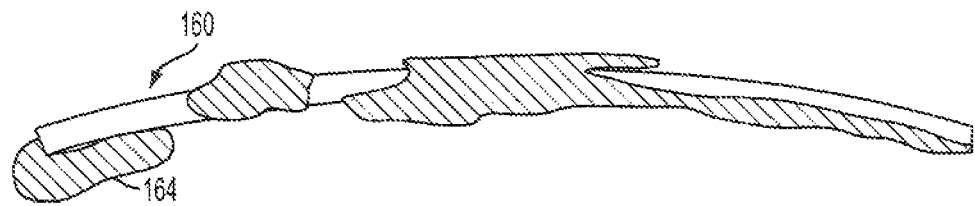

As illustrated in prior art FIG. 9B, conventional catheters such as PICCs can often times accumulate blood components (platelets and thrombus) on surfaces, sometimes as early as during the initial insertion procedure as the catheter is introduced into the vein and advanced towards a target site. Thrombus accumulation 164 can be common near a catheter tip, as low pressure pockets cause blood flow to swirl into the catheter tip surface, and as reflux draws blood into the distal end of the catheter lumen. As thrombus begins to accumulate at surfaces near the catheter tip and within the catheter lumen during insertion, the acquired P-wave signal can become noisy or muted. It is believed that thrombus formations at the tip of the catheter or within the catheter lumen contribute to the noise in the P-wave signal due to the P-wave refracting against the solid formations. Further, if thrombus is blocking or otherwise minimizing electrode exposure, the signal can lose strength and become muted. This interference can result in a low resolution IV ECG signal, becoming problematic for tip location systems which a minimum resolution in ECG waveforms to accurately measure and track changes in the P-wave.

Catheters such as those described in Lareau et al., U.S. Pat. No. 8,603,070, incorporated herein by reference, comprise a fluoropolymer additive with specific compositions and/or purity levels, to achieve an anti-thrombogenic effect. One example of a catheter comprising fluoropolymer additives to achieve this anti-thrombogenic effect is the BioFlo PICC (AngioDynamics, Inc., Latham, N.Y.). PICC catheters according to embodiments of the present invention may be characterized by a wall thickness between the outer surface and the lumen of 0.005 to 0.050 inches. In some embodiments, the catheter comprises a polymeric material comprising polyurethane and additives, which comprise a radiopaque material and a fluoropolymer comprising terminal polyfluoro-oligomeric groups. The additives comprise up to about 44 weight percent of said polymeric material. In other embodiments, the catheter comprises a polymeric material comprising a fluoropolymer comprising terminal polyfluoro-oligomeric groups, wherein the fluoropolymer is characterized by a polystyrene equivalent weight average molecular weight (Mw) greater than 13,000 Daltons (13 kDa).

Figure 10:
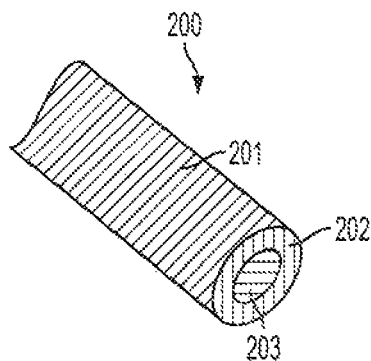
FIG. 10 is a perspective view of a catheter tip according to an embodiment of the invention.
Figure 11A:
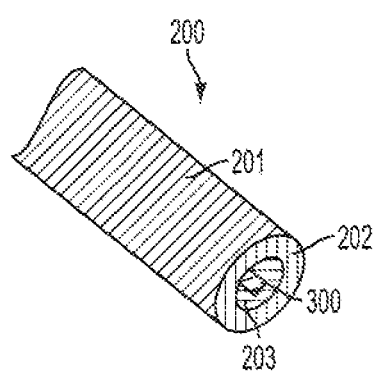
FIGS. 11A and 11B show a catheter tip and stylet system according to an embodiment of the invention.
Figure 11B:
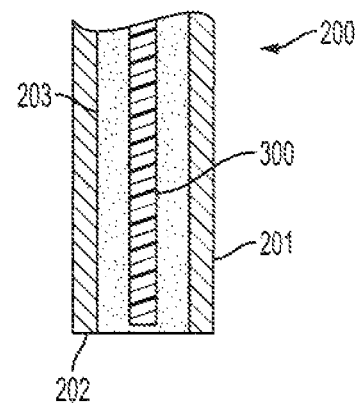

As shown in FIG. 10, a PICC 200 with fluoropolymer additives, such as those described in Lareau et al. will have anti-thrombogenic properties present at the outer surface 201, the distal tip surface 202, and the inner luminal surface 203. The PICC is manufactured with an admixture of a base polymer and a surface modifying fluoropolymer additive. Since the anti-thrombogenic fluoropolymer additives are integral to the catheter shaft, the distal tip surface 202 will retain the anti-thrombogenic properties even after the distal tip of the catheter is trimmed. As shown in FIGS. 11A and 11B, outer surfaces 201, distal tip surfaces 202 and inner luminal surfaces 203 adjacent to the stylet 300 have anti-thrombogenic properties. Since anti-thrombogenic properties are present on all exterior surfaces, specifically surfaces adjacent to the stylet, thrombus formation is minimized and the stylet 300 can better maintain acquisition of a high resolution P-wave with high signal to noise ratios and minimized thrombus related interference throughout the PICC placement procedure. This is advantageous since PICCs are often trimmed prior to insertion, and anti-thrombogenic fluoropolymer additives integral to the catheter shaft allow for the retention of an anti-thrombogenic distal tip surface 202. Therefore, catheter kits or systems that include the combination of the described anti-thrombogenic catheters and an IV signal acquisition stylet offer an advantageous combination for ECG based tip location systems. Alternative embodiments including catheters coated or impregnated with anti-thrombogenic materials will also see improved signal acquisition. In an alternative embodiment, a column of saline can be present within the catheter lumen to improve the propagation of the P-wave signal. If a column of saline is used instead of a stylet, catheters having fluoropolymer additives integral to the catheter shaft are nonetheless advantageous since distal inner luminal surfaces 203, the distal tip surfaces 202, and exterior surfaces 201 could still accumulate thrombus where blood is in contact with the catheter surface.

What is claimed is:

1. A method for placing a peripherally inserted catheter tip using an ECG search window, the method comprising:
    acquiring a plurality of surface ECG signals from at least one surface ECG electrode;
    generating a signal averaged surface ECG signal from the plurality of surface ECG signals;
    determining a first fiducial point by identifying an extremum of a R wave;
    establishing a first ECG search window between first and second predetermined values offset from the first fiducial point;
    determining a second fiducial point by identifying an extremum in the first ECG search window;
    determining a search window beginning value by identifying a local extremum on a first side of the second fiducial point, and determining a search window ending value by identifying a local extremum on a second side of the second fiducial point;
    establishing a second ECG search window between the search window beginning value and the search window ending value so that the second ECG search window is narrower than the first ECG search window; and
    applying the second ECG search window to an intravascular ECG signal acquired from an intravascular ECG electrode coaxially surrounded by the peripherally inserted catheter tip.

2. The method of claim 1, wherein the first predetermined value is 40 ms prior to the first fiducial point, and the second predetermined value is 220 ms prior to the first fiducial point.

3. The method of claim 1, wherein the plurality of surface ECG signals is measured over 15 heartbeats.

4. The method of claim 1, wherein the local extremum on the first side of the second fiducial point is a first occurrence of a local extremum left of the second fiducial point, and wherein the local extremum on the second side of the second fiducial point is a first occurrence of a local extremum right of the second fiducial point.

5. The method of claim 1, wherein the step of acquiring a plurality of surface ECG signals from at least one surface ECG electrode further comprises acquiring a plurality of surface ECG signals from a plurality of surface ECG electrodes.

6. The method of claim 5, wherein the plurality of surface ECG electrodes is three surface ECG electrodes.

7. The method of claim 4, wherein the local extremum on the first side of the second fiducial point and the local extremum on the second side of the second fiducial point is determined using a first derivative test.

8. A method for assisting with placement of a peripherally inserted catheter tip within a patient, the method comprising:
    acquiring a plurality of surface ECG signals from at least one surface ECG electrode;
    generating a signal averaged surface ECG signal from the plurality of surface ECG signals;
    determining a first fiducial point by identifying an extremum in the signal averaged surface ECG signal;
    establishing a first ECG search window between first and second predetermined values offset from the first fiducial point;
    determining a second fiducial point by identifying an extremum within the first ECG search window;
    determining a search window beginning value by identifying a local extremum on a first side of the second fiducial point, and determining a search window ending value by identifying a local extremum on a second side of the second fiducial point;
    establishing a second ECG search window between the search window beginning value and the search window ending value so that the second ECG search window is narrower than the first ECG search window;
    acquiring an intravascular ECG signal from an intravascular electrode near the peripherally inserted catheter tip,
    applying the second ECG search window to the intravascular ECG signal to generate an intravascular ECG search window;
    establishing the intravascular ECG search window by offsetting the search window beginning value and the search window ending value from an intravascular ECG signal fiducial point, wherein the intravascular ECG signal fiducial point is an extremum of an R-wave; and
    providing user feedback about the placement of the peripherally inserted catheter tip based on changes in the intravascular ECG signal within the intravascular ECG search window.

9. The method of claim 8, wherein the step of monitoring changes in the intravascular ECG signal within the intravascular ECG search window further comprises:
    determining a first amplitude based on an extremum of the intravascular ECG signal within the intravascular ECG search window with the intravascular electrode at a first position within the patient, and
determining a second amplitude based on an extremum of the intravascular ECG signal within the intradardial ECG search window with the intravascular electrode at a second position within the patient.

10. The method of claim 9 further comprising:
    providing user feedback to advance the catheter tip when the second amplitude is greater than the first amplitude.

11. The method of claim 10, wherein at least one of the first amplitude and the second amplitude are determined from signal averaged intravascular ECG signals measured over a plurality of heartbeats.

12. The method of claim 9 further comprising:
    providing user feedback to pull back the catheter tip when the second amplitude is less than the first amplitude.

13. The method of claim 12, wherein at least one of the first amplitude and the second amplitude are determined from signal averaged intravascular ECG signals measured over a plurality of heartbeats.

14. The method of claim 9, wherein the step of generating the intravascular ECG search window comprises identifying an extremum in the intravascular ECG signal.

15. The method of claim 8, wherein the intravascular ECG signal within the intravascular ECG search window is a P-wave.

16. The method of claim 8, wherein the intravascular electrode comprises at least one of a column of fluid and a stylet.

17. A method for placing a peripherally inserted catheter tip using an ECG search window, the method comprising:
   acquiring a plurality of surface ECG signals from at least one surface ECG electrode;
   generating a signal averaged surface ECG signal from the plurality of surface ECG signals;
   determining a first fiducial point by identifying an extremum within the signal averaged surface ECG signal;
   establishing a first ECG search window between first and second predetermined values offset from the first fiducial point;
   determining a second fiducial point by identifying an extremum of a P-wave;
   determining a search window beginning value by identifying a local extremum on a first side of the second fiducial point, and determining a search window ending value by identifying a local extremum on a second side of the second fiducial point;
   establishing a second ECG search window between the search window beginning value and the search window ending value so that the second ECG search window is narrower than the first ECG search window; and
   applying the second ECG search window to an intravascular ECG signal acquired from an intravascular ECG electrode coaxially surrounded by the peripherally inserted catheter tip.

\* \* \* \* \*